United States Patent
Rouiller et al.

(10) Patent No.: US 7,125,252 B2
(45) Date of Patent: Oct. 24, 2006

(54) DRILLING INSTRUMENT IN PARTICULAR FOR DRILLING DENTAL ROOT CANALS

(75) Inventors: Jean-Claude Rouiller, 49, rue Abraham-Robert, CH-2300, La Chaux-de-Fonds (CH); Olivier Breguet, Le Locle (CH)

(73) Assignee: Jean-Claude Rouiller(CH)

( * ) Notice: Subject to any disclaimer, the term of this patent is extended or adjusted under 35 U.S.C. 154(b) by 463 days.

(21) Appl. No.: 10/468,498

(22) PCT Filed: Feb. 19, 2002

(86) PCT No.: PCT/CH02/00098

§ 371 (c)(1),
(2), (4) Date: Aug. 19, 2003

(87) PCT Pub. No.: WO02/065938

PCT Pub. Date: Aug. 29, 2002

(65) Prior Publication Data

US 2004/0131993 A1    Jul. 8, 2004

(30) Foreign Application Priority Data

Feb. 20, 2001 (FR) .................................. 01 02452

(51) Int. Cl.
*A61C 5/02* (2006.01)

(52) U.S. Cl. ...................................... 433/102; 408/230

(58) Field of Classification Search ................ 433/102, 433/165, 81, 224; 83/651.1; 606/80; 408/230; 175/394
See application file for complete search history.

(56) References Cited

U.S. PATENT DOCUMENTS

| 3,258,797 | A | * | 7/1966 | Budd | .................... 470/204 |
| 4,260,379 | A | | 4/1981 | Groves et al. | |
| 4,496,011 | A | * | 1/1985 | Mazo et al. | .................... 175/19 |
| 4,549,616 | A | * | 10/1985 | Rumpp et al. | ............... 175/394 |
| 5,632,620 | A | * | 5/1997 | Musikant et al. | ............ 433/102 |
| 5,735,689 | A | * | 4/1998 | McSpadden | ................ 433/102 |
| 5,876,202 | A | * | 3/1999 | Berlin | .................... 433/102 |
| 6,074,209 | A | | 6/2000 | Johnson | |
| 6,299,445 | B1 | * | 10/2001 | Garman | ..................... 433/102 |
| 6,382,973 | B1 | * | 5/2002 | Murai et al. | ................ 433/102 |

FOREIGN PATENT DOCUMENTS

WO    WO0059399    12/2000

* cited by examiner

*Primary Examiner*—John J Wilson
(74) *Attorney, Agent, or Firm*—Gibbons, Del Deo, Dolan, Griffinger and Vecchione

(57) ABSTRACT

The invention concerns a drilling instrument (10), in particular for drilling dental root canals comprising a base (11) and a guide section (13) as well as a polygonal cutting section (12). Said cutting section includes several helical cutting edges (17) defining an envelope (15). The flutes (14), which are the surfaces linking in the cutting edges, are cut out such that part of them define clearance zones (16a) alternately arranged between the drilling zones (16b). In the central part of a clearance zone (16a), the cutting edges (17) are all arranged recessed inside the envelope (15), in the central part of the drilling zone (16b), said cutting edges are all arranged on the envelope, and in a zone intermediate between a clearance zone (16a) and an adjacent drilling zone (16b), at least one cutting edge is on the envelope and at least one cutting edge is recesses inside the envelope.

10 Claims, 2 Drawing Sheets

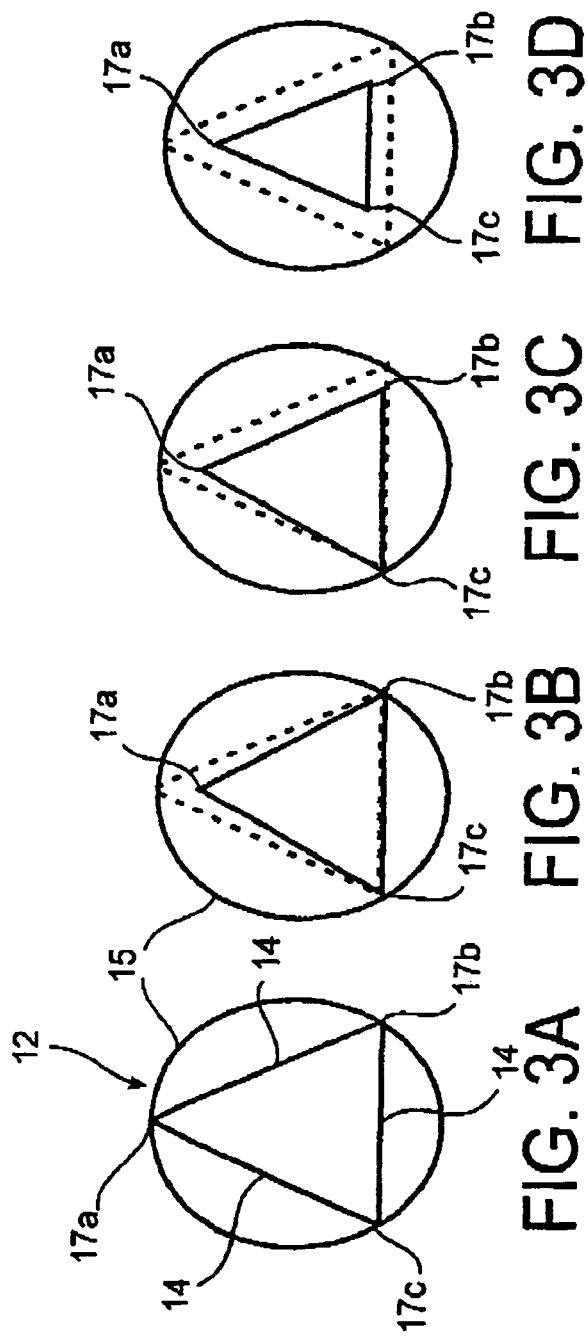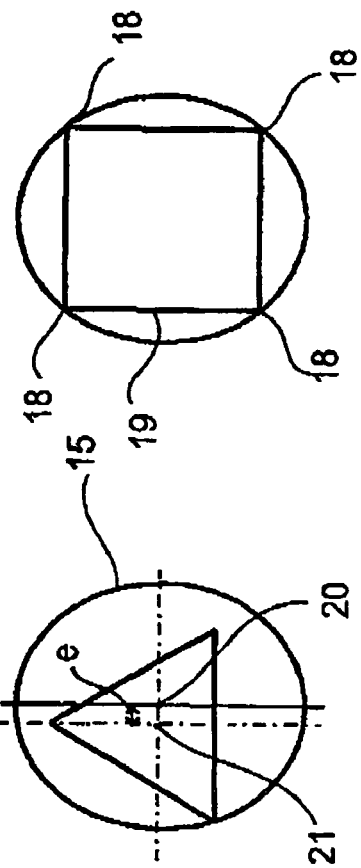

DRILLING INSTRUMENT IN PARTICULAR FOR DRILLING DENTAL ROOT CANALS

This application is a National Stage Application of PCT/CH02/00098 which claims priority from FR 01/02452 filed Feb. 20, 2001.

FIELD OF THE INVENTION

The present invention concerns a drilling instrument, in particular for drilling dental canals in the framework of dental root treatment, this instrument including a base, a cutting section and a guiding section, the cutting section being defined by an envelope cylindrical or conical in shape, this cutting section being provided with clearance zones, placed so that they are set back relative to the envelope, alternating with drilling zones placed on the envelope.

BACKGROUND OF THE INVENTION

Currently, most of the dental canal drilling instruments have a cutting part called a cutting section with a conical envelope and including one or more cutting edges wound up into a helix along this cutting part.

This helical shape is indispensable for removal of debris from teeth around the outside of the root. During use, the conical part may undergo a coating phenomenon when the instrument is introduced into the root canal and when it is carried along in rotation. It may happen that it becomes bound in the root canal. For this reason, it is recommended to use such an instrument only with manual axial movement possibly with a slight movement in rotation alternating in one direction and in the reverse direction. Otherwise, the instrument may be blocked in the tooth and break. Breaking the instrument may cause serious consequences given that a dental canal is narrow and that access to it is difficult.

There are certain instruments for which the tendency towards binding has been partially eliminated. In particular, this has been obtained by greatly blunting the cutting angles. This type of instrument may be used with a rotating drive motor turning at low speed so as not to deform the natural path of the canal while enlarging it.

The fact that the cutting edges may be blunted presents a drawback for several reasons. On the one hand, the cutting work necessary to enlarge the dental canal is carried out with difficulty. On the other hand, the friction between the blunted edges and the walls of the canal causes significant working torque, which may also cause the instrument to break. In order to avoid this risk, it is necessary to use a whole range of instruments with different conicities, those having the greatest conicity being used first. In this case, the coating effect is eliminated and the restraints due to friction caused on the instrument remain less than the breaking limit. However, the work is only applied to a delimited part of the dental canal.

With most of the known motorized drive instruments the gain in time relative to the manual method is not certain and the risks of breaking remain high.

Various instruments of this type have been the object of patents. The U.S. Pat. No. 6,074,209 precisely describes one of these instruments in which the edges are rounded. It includes zones with narrow cross section which alternate with zones of larger cross section. The zones of narrow cross section are obtained by grinding the part in predetermined places of a blank in which the section is initially constant if the instrument is cylindrical, or regularly decreasing if the instrument is generally conical in shape which causes passages between the zones with narrow cross section and zones with larger cross section to sharp transverse edges which risk catching on the walls of the canal and blocking the instrument.

The international application published as WO 00/59399 describes an instrument of this type made by twisting an elongated piece with a general conical shape and in which the cross section is rhomboidal in shape. It is also the case with the instrument described in U.S. Pat. No. 4,260,379. The rhombus has a large diagonal and a small diagonal, the instrument is made twisting a piece in which the section is a rhomboid and includes alternating zones of reduced cross section and larger cross section corresponding respectively to the small and large diagonal of the rhombus. The zones with different section are not moved along the instrument but they are angularly moved by 90 degrees. It is noted that this geometry does not allow avoidance of the binding phenomenon of the instrument and that certain restraints exerted on this instrument could cause its breaking.

SUMMARY OF THE INVENTION

The present invention proposes to improve the drawbacks of the drilling instruments of prior art by offering an instrument in which the risk of binding is eliminated while maintaining a relatively low torque, thus avoiding premature fatigue.

These goals are reached by an instrument as defined in the preamble and characterized in that the cutting section is polygonal in cross section and includes sharp edges, in that in the central part of a clearance zone said edges are all placed so as to be set back within said envelope, in that in the central part of a drilling zone, these edges are all placed on said envelope and in which, in an intermediate zone between a clearance zone and an adjacent drilling zone, at least one edge is on the envelope and at least one edge is set back within the envelope.

According to a preferred embodiment, the axis of the cutting section is moved forward relative to the axis of said envelope. This axis of the cutting section is helicoidal and is wound up into a helix around the rectilinear axis of the envelope, in order to make the removal zones deeper and more effective.

Particularly advantageously, an intermediate zone located between the central part of a clearance zone and the central part of an adjacent drilling zone is divided into n segments where n corresponds to the number of edges of the cutting section, and along each of these segments the number of edges placed on the envelope is increased by a unit in the direction going from a clearance zone towards the adjacent drilling zone.

In the specific case where said cutting section has a triangular cross section, an intermediate zone located between the central part of a clearance zone and the central part of an adjacent drilling zone is preferably divided into three segments, and along each of these segments the number of edges placed on the envelope goes successively from zero to one, then to two and finally three in the direction going from a clearance zone towards the adjacent drilling zone.

According to a particularly advantageous embodiment, at least one flute, which is the surface delimited by two edges of the cutting section, is overtrimmed relative to the others so as to form said clearance zones.

In the case where the cutting section includes four cutting edges, these edges define four flutes which are placed at approximately right angles.

Preferentially, said instrument is used in the odontology field and the dimension of the clearance zone are 0.1 mm less than that of the drilling zone.

When the cross section of the cutting section is triangular, its shape is preferentially that of an equilateral triangle.

BRIEF DESCRIPTION OF THE DRAWINGS

The present invention and its advantages will be better understood in reference to the following description of different embodiments of the invention and to the attached drawings in which:

FIGS. 3A and 3D are cutaway views along lines A—A and B—B of FIG. 2, respectively, illustrating the variation in the contour of the cutting section, FIGS. 3B and 3C being views intermediate between these two positions;

FIG. 4 is a cutaway view illustrating a specific embodiment of the cutting section, and FIG. 5 represents another shape for production of the instrument according to the invention.

DETAILED DESCRIPTION OF THE INVENTION

Figure 1:
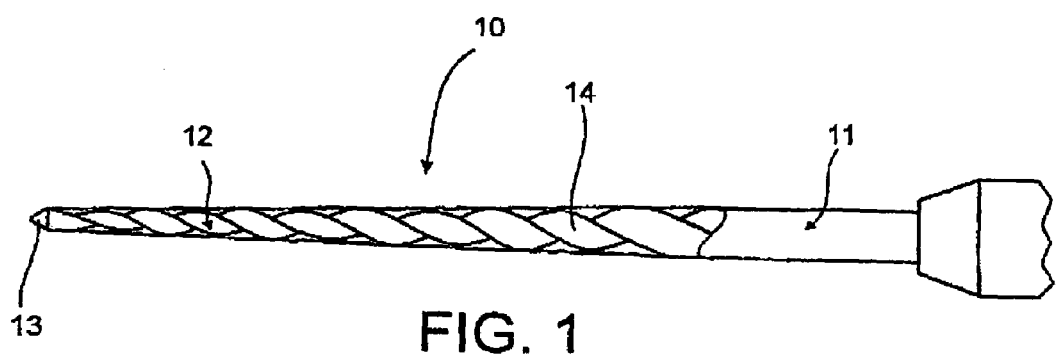
FIG. 1 is a view of the entire instrument according to the present invention.
Figure 2:
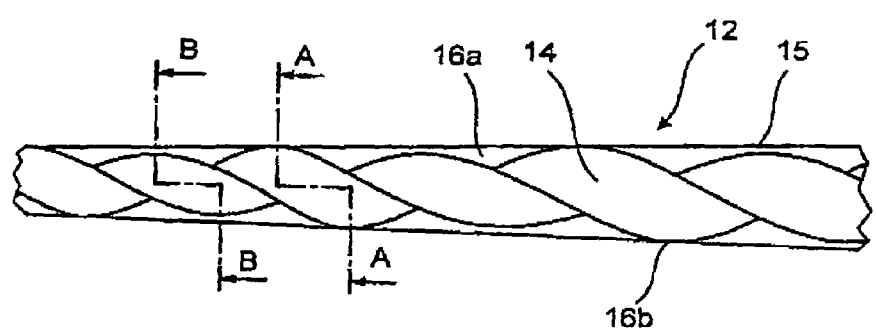
FIG. 2 is an enlarged view of a central part of the instrument of FIG. 1 and corresponding to the cutting section.

In reference to the figures, the drilling instrument 10 according to the present invention includes a base 11, a cutting section 12 and a guiding section 13. Base 11 is conventional and may have a cylindrical or conical shape, with a circular or polygonal cross section, especially a square or triangular one. The guiding section 13 is also formed conventionally and is ended by a rounded point allowing easy introduction into the drilling to be treated [sic] and in particular into a dental canal. In the example illustrated by FIG. 1, the guiding section 13 presents a certain conicity that allows the operator to easily follow the natural tracing of the canal with a view to enlarging it by means of the cutting section 12.

The cutting section 12 has a new shape relative to the cutting sections of existing instruments. In the illustrated examples, it is polygonal in section and includes sharp edges. More specifically, in the example illustrated by FIGS. 1 to 4, it includes a triangular cross section forming sharp edges 17a, 17b and 17c, defining three flutes 14 helicoidal in shape which are placed within an approximately truncated envelope 15, a flute being the surface bounded by two edges of the cutting section 12. This cutting section 12 includes clearance zones 16a placed so that it is set back relative to the envelope 15 and which alternate with the drilling zones 16b placed on the envelope 15, the dimension of the clearance zone 16a being 0.1 mm less than that of the drilling zone 16b.

As shown in FIG. 3A, which is a cutaway view in the central part of the drilling zone, the edges 17a, 17b and 17c are all placed on said envelope 15 and, as shown in FIG. 3D, which is a cutaway view in the central part of a clearance zone, these edges are all placed so that they are set back within said envelope 15. FIGS. 3B and 3C show that in an intermediate zone between the clearance zone and an adjacent drilling zone, at least one edge 17b and/or 17c is on the envelope and at least one edge 17a and/or 17b is set back within the envelope 15.

Since the cross section of the cutting section 12 has a polygonal shape, the number of its edges being n, and considering that an intermediate zone located between the central part of a clearance zone 16a and the central zone of an adjacent drilling zone 16b is divided into n segments, when one moves along each of these segments, the number of edges placed on the envelope 15 is increased by a unit in the direction going from a clearance zone towards the adjacent drilling zone. In this way, the passage of the edges from their position on the envelope 15 towards a position that is set back relative to this envelope is carried out continuously and uniformly.

When said cutting section 12 has a triangular cross section, an intermediate zone located between the central part of a clearance zone 16a and the central part of an adjacent drilling zone 16b is divided into three segments and along each of these segments, the number of edges placed on the envelope goes successively from zero to one, then to two and finally to three in the direction going from a clearance zone 16a towards an adjacent drilling zone 16b.

To create this geometry by means of grinding equipment, at least one flute 14 is overtrimmed locally compared with others so as to form said clearance zones 16a. At least one part of one of the flutes is trimmed so that it is not tangential to the envelope.

A variant illustrated by FIG. 4 makes it possible to again increase the effectiveness of the clearance zones. According to this embodiment, the axis 20 of envelope 15 is moved a distance e from axis 21 of the cutting section 12. Axis 20 of the envelope is rectilinear and axis 21 of the cutting section is helicoidal and is wound up into a helix around axis 20. The embodiment makes it possible to deepen the clearance zones and to make them more effective for carrying material during treatment.

In the example illustrated by FIG. 5, the cutting section 12 is rectangular in cross section and therefore includes four sharp edges 16 which define four flutes 19 placed approximately at right angles. In this embodiment, two opposing flutes may be overtrimmed.

These embodiments present numerous advantages relative to similar instruments of the prior art. On the one hand, the instrument is easy to machine since the existence of a clearance zone spaced between the envelope and one or more flutes practically does not modify the production procedure which is based on the relative displacement of the abrasive wheels and the blank of the instrument in an automatic and programmed way.

In addition, they absolutely avoid any risk of binding of the instrument. Thus, it is possible and even desirable to keep a sharp cutting edge. This makes excellent machining of the material possible while avoiding heating of the instrument and while maintaining a relatively low torque. The lifetime of the instrument is thus found to be increased and the risk of breakage is greatly decreased.

The decrease of the torque also makes it possible to use a relatively flexible instrument which ensures it good guiding into a curved dental canal.

As the risk of binding is zero, it is not necessary to use a large range of instruments with different conicities which decreases the cost of the material necessary for the treatment on the one hand, and the length of treatment on the other.

INDUSTRIAL APPLICATION POSSIBILITIES

The present invention has been described essentially in an application in odontology, with a drill essentially conical or cylindrical in shape. Other shapes of drills could also be used. In particular, it is possible to apply the invention to drills of known types with the names "Gate," "Peeso" or cylindrical drills, as well as for known cutters for pins, with an overtrimmed shaft or "fissure."

The helical pitch of the flutes, their number and the dimension of the clearance zones are not limited and it is possible to modify them without leaving the scope of the present invention.

It is also possible to use the instrument that is the object of the invention in fields other than odontology, especially in surgery and in particular in orthopedics, as well as in fields such as mechanics for working metals or synthetic materials, carpentry or working with wood and similar materials. This especially makes it possible to make drills for manual use in which there is no risk of binding.

What is claimed is:

1. Endodontic instrument comprising: a base (11), a cutting section (12) and a guiding section (13), the cutting section being defined by an envelope (15) of cylindrical or conical shape, this cutting section being provided with clearance zones (16a), located so that said clearance zones are set back relative to the envelope (15), alternating with drilling zones (16b) placed on said envelope, the cutting section (12) is a polygonal in cross section and includes sharp edges, and in a central part of a clearance zone (16a) said edges are all placed so that said edges are set back from the envelope (15), wherein the central part of a drilling zone (16b), said edges are all placed on said envelope and in a zone intermediate between a clearance zone (16a) and an adjacent drilling zone (16b), at least one edge is on the envelope and at least on edge is set back from the envelope.

2. Endodontic instrument according to claim 1, wherein an axis (21) of the cutting section (12) is moved relative to an axis (20) of said envelope (15).

3. Endodontic instrument according to claim 2, wherein the axis (21) of the cutting section (12) is helicoidal and turns around the rectilinear axis (20) of the envelope (15).

4. Endodontic instrument according to claim 1, wherein an intermediate zone located between the central part of a clearance zone (16a) and the central part of an adjacent drilling zone (16b) is divided into n segments where n corresponds to the number of edges of the cutting section (12), and in that along each of said segments the number of edges placed on the envelope (15) is increased by a unit in the direction going from a clearance zone (16a) towards the adjacent drilling zone (16b).

5. Endodontic instrument according to claim 4, in which said cutting section (12) has a triangular cross section, wherein an intermediate zone located between the central part of a clearance zone (16a) and the central part of an adjacent drilling zone (16b), is divided into three segments and in that along each of these segments, the number of edges placed on the envelope goes successively from zero to one, then to two and finally to three in the direction going from a clearance zone (16a) toward the adjacent drilling zone (16b).

6. Endodontic instrument according to claim 5, wherein at least one flute (14), which is the surface bounded by two edges of the cutting section (12), is overtrimmed relative to the others so as to form said clearance zones (16a).

7. Endodontic instrument according to claim 1, wherein the cutting section (12) includes four cutting edges (18), which define four flutes (17) placed approximately at right angles.

8. Endodontic instrument according to claim 1, used in the field of odontology, wherein a dimension of the clearance zone (16a) is 0.1 mm less than that of the drilling zone (16b).

9. Endodontic instrument according to claim 1, wherein the cutting section (12) has a cross section with the shape of an equilateral triangle.

10. Endodontic instrument according to claim 1, wherein the cutting section (12) has a cross section that is approximately square in shape.

* * * * *